(12) United States Patent
Kim (10) Patent No.: US 8,444,658 B2
(45) Date of Patent: May 21, 2013

(54) HYDRODYNAMIC SUTURE PASSER

(76) Inventor: Andrew C. Kim, Temecula, CA (US)

( * ) Notice: Subject to any disclaimer, the term of this patent is extended or adjusted under 35 U.S.C. 154(b) by 726 days.

(21) Appl. No.: 10/883,742

(22) Filed: Jul. 6, 2004

(65) Prior Publication Data

US 2005/0033323 A1    Feb. 10, 2005

Related U.S. Application Data (63) Continuation-in-part of application No. 10/614,653, filed on Jul. 7, 2003, now Pat. No. 7,699,857.

(51) Int. Cl.
*A61B 17/04* (2006.01)
*A61B 17/12* (2006.01)

(52) U.S. Cl.
USPC .......................................................... 606/144

(58) Field of Classification Search
USPC ............... 606/144, 139, 145–148; 604/11, 604/16, 150, 154, 159, 502, 506, 522
See application file for complete search history.

(56) References Cited

U.S. PATENT DOCUMENTS

| | | | |
|---|---|---|---|
| 989,234 A * | 4/1911 | Davis | 606/146 |
| 3,638,653 A | 2/1972 | Berry | |
| 3,703,174 A | 11/1972 | Smith | |
| 3,840,017 A | 10/1974 | Violante | |
| 4,224,947 A | 9/1980 | Fukuda | |
| 4,767,415 A * | 8/1988 | Duffy | 604/232 |
| 4,890,615 A * | 1/1990 | Caspari et al. | 606/146 |
| 5,021,059 A * | 6/1991 | Kensey et al. | 606/213 |
| 5,236,443 A * | 8/1993 | Sontag | |
| 5,376,081 A * | 12/1994 | Sapienza | 604/207 |
| 5,515,871 A * | 5/1996 | Bittner et al. | 128/898 |
| 5,562,683 A | 10/1996 | Chan | |
| 5,562,685 A * | 10/1996 | Mollenauer et al. | 606/144 |
| 5,569,270 A * | 10/1996 | Weng | 606/144 |
| 5,618,290 A | 4/1997 | Toy et al. | |
| 5,681,331 A | 10/1997 | De La Torre et al. | |
| 5,810,832 A * | 9/1998 | Blasingame et al. | 606/103 |

(Continued)

FOREIGN PATENT DOCUMENTS

| WO | WO 2004/034867 | * | 4/2004 |
|---|---|---|---|
| WO | WO 2005/007201 A2 | | 1/2005 |
| WO | WO 2005/007201 A3 | | 1/2005 |

OTHER PUBLICATIONS

International Preliminary Report of Patentability for PCT/US2004/021586 filed on Jul. 6, 2004.

(Continued)

*Primary Examiner* — Gary Jackson
*Assistant Examiner* — Lindsey Bachman
(74) *Attorney, Agent, or Firm* — James W. Chang (57) ABSTRACT

A hydrodynamic suturing instrument, comprising an elongated cannulated suturing needle having a distal end configured to carry a suture through tissue and a proximal end adapted to connect to a syringe barrel and a lumen extending form said proximal end to an opening at the distal end for having a size for the passage of a suture, the opening at the distal end configured to receive a suture extending from the lumen along an outer surface of the needle wherein a sharp point extends forward of the suture. A companion instrument includes forceps having a distal end with jaws and a proximal end with a cannula extending from the proximal end to the distal end for passage of the needle, and the jaws having an opening enabling passage of the needle through tissue grasped in the jaws.

5 Claims, 8 Drawing Sheets

U.S. PATENT DOCUMENTS

| | | | |
|---|---|---|---|
| 5,964,735 A | 10/1999 | Alexander | |
| 6,162,202 A * | 12/2000 | Sicurelli et al. | 604/272 |
| 6,299,590 B1 * | 10/2001 | Luscher et al. | 604/11 |
| 6,440,098 B1 * | 8/2002 | Luscher | 604/57 |
| 6,679,895 B1 * | 1/2004 | Sancoff et al. | 606/144 |
| 6,699,285 B2 * | 3/2004 | Zapata | 623/6.63 |
| 6,755,831 B2 * | 6/2004 | Putnam et al. | 606/311 |
| 7,077,826 B1 * | 7/2006 | Gray | 604/171 |
| 7,081,125 B2 | 7/2006 | Edwards et al. | |
| 2005/0033323 A1 | 2/2005 | Kim | |
| 2006/0155307 A1 | 7/2006 | Rosch | |

OTHER PUBLICATIONS

International Search Report for PCT/US2009/053496 filed on Aug. 11, 2009.

International Search Report and Written Opinion of the International Searching Authority, for PCT/US2009/053496 filed on Aug. 11, 2009.

International Preliminary Report on Patentability for PCT/US2009/053496 filed on Aug. 11, 2009.

* cited by examiner

HYDRODYNAMIC SUTURE PASSER

CROSS REFERENCE TO RELATED APPLICATIONS

This application is a continuation-in-part of U.S. patent application Ser. No. 10/614,563 filed Jul. 7, 2003 now U.S. Pat. No. 7,669,857, from which priority is claimed under 35 U.S.C. §120 and which is incorporated herein by reference in its entirety.

FIELD OF THE INVENTION

The present subject matter relates to surgical instruments and pertains particularly to an apparatus and method for passing sutures through tissue.

BACKGROUND OF THE INVENTION

Recently developed arthroscopic, endoscopic, and laparoscopic surgical techniques have reduced the pain and discomfort normally experienced by patients undergoing traditional "open" surgery and decreases the recovery time and scarring common to such traditional surgery. These techniques are commonly performed in confined spaces, wherein one or more tubes may be inserted in the patient, and surgical instruments and materials are moved in to the surgery site through the tube or tubes. Accordingly, these surgical techniques require smaller incisions in a patient than traditional surgery in which an incision is made in a patient to open the site to be operated on to relatively unrestricted access.

Due to these smaller incisions, the suturing of tissue under the constraints of arthroscopic, endoscopic, or laparoscopic surgery, or any other form of non-open surgery, is difficult with the tools and instruments presently available. While many instruments have been proposed to solve this problem in the past, such instruments have been found to possess a number of drawbacks.

The presently available instruments or suture passers generally fall into two main categories. The first type of device is designed to propel a relatively rigid, usually monofilament, suture with mechanical force through a cannula or hollow needle through the tissue. These devices cannot pass more flexible, braided sutures through the tissue.

The second type of presently available device uses a solid needle or wire with a closed or open eyelet to carry the suture through tissue. However, a device with a closed eyelet provides for difficulty in removing the suture from the eyelet. Devices with an open eyelet may include a notch from which the suture can be removed without having to move a length of suture through a closed eyelet to correct this problem. However, the notch comprises an exposed surface which can catch on tissue, making passage through the tissue difficult. These devices also require other instruments to grasp and pull the suture free from the needle or wire.

A number of prior patents describe such presently known instruments. For example, U.S. Pat. Nos. 4,890,615 to Caspari et al.; 919,138 to Drake et al.; U.S. Pat. No. 3,840,017 to Violante; U.S. Pat. No. 4,224,947 to Fukuda; and U.S. Pat. No. 4,643,178 to Nastari et al. disclose suturing instruments wherein sutures are passed through hollow needles after the needles penetrate through tissue to be sutured. However, the use of these instruments has the disadvantage that the suture material must be grasped by an instrument not useful in arthroscopic surgery.

Similarly, U.S. Pat. No. 4,493,323 to Albright et al. and U.S. Pat. Nos. 4,602,635 and 4,621,640 to Mulhollan et al. disclose instruments for internal suturing in confined space, but require multiple instrument manipulation and movement of needles carrying sutures entirely through the tissue to be sutured. The Albright et al. patent in particular discloses a pair of needles that are forced outwardly through the end of a tube by a plunger to penetrate and extend through the tissue to be sutured. The needles are grasped and pulled by a surgeon to position a suture thread loop attached to the needles. Likewise, the '635 patent discloses an instrument for tying knots in sutures in a manipulation area external to the body after sutures are passed through the tissue. The knots are then forced into place adjacent to the tissue by another instrument. The '640 patent similarly discloses a curved needle carried by a pivoting head movable to set the needle in the tissue to be sutured. The needle is then released, the instrument is withdrawn, and another instrument is inserted to pull the needle through.

U.S. Pat. Nos. 1,815,725 to Pilling et al.; U.S. Pat. No. 3,470,875 to Johnson; U.S. Pat. No. 3,842,840 to Schweizer; U.S. Pat. No. 3,946,740 to Bassett; and U.S. Pat. No. 4,164,225 to Johnson et al. disclose suturing instruments having pivoted, scissor-like arms with a needle at the end of an arm forced through tissue to be sutured. The end of the arm is next forced into the end of another arm, where the suture is grasped or clamped. The instruments are of a structural design that is not practical in arthroscopic surgery.

U.S. Pat. No. 4,312,337 to Donohue discloses an instrument for drilling and wiring bones. Scissor-like arms carry cannula sections through which a wire is passed, the wire being cut and tied after the cannula sections are withdrawn. The structure is such that it does not permit the instrument to be used in arthroscopic surgery.

In addition to their inconvenience in use in arthroscopic surgery, these prior art devices present other drawbacks as well. For example, the '615 patent to Caspari et al. noted above discloses pushing a suture through a hollow needle. A suture feed mechanism adjacent to a proximal end of the needle (the end of the needle closer to a surgeon's hand) comprises rollers which grasp the suture and push it toward a distal end of the needle. Pushing the suture through the hollow needle requires a suture stiff enough to be pushed, such as, for example, a monofilament suture. However, soft, braided sutures are easier for a surgeon to manipulate and tie and are thus generally preferable. Soft braided sutures are not typically suited to being pushed from a proximal end to a distal end of a hollow needle.

The presently known suturing instruments and methods, then, are of limited effectiveness for use in closely confined spaces such as sites of arthroscopic surgery. Accordingly, there remains a need in the art for suturing instruments and methods designed for and effective in providing sutures in the closely confined spaces provided by, e.g. arthroscopic surgery. The present subject matter addresses this need.

SUMMARY OF THE INVENTION

A primary aspect of embodiments of the present subject matter relates to a hydrodynamic suturing instrument comprising an elongated cannulated suturing needle having a distal end configured to pass a suture through tissue and a proximal end adapted to connect to a syringe barrel or other suction device. A lumen for the passage of a suture extends from the proximal end to an opening at the distal end. The distal end is configured with a sharp point extending forward from an opening to said lumen, the opening being configured to receive a suture extending from said lumen along an outer surface of the needle wherein said sharp point extends forward of the suture. A suture is loaded in to the syringe through the needle by drawing it in with a liquid. The suture is expelled from the needle after passage through tissue.

An additional aspect of embodiments of the present subject matter comprises a forceps having a distal end with jaws and a proximal end and a cannula extending from the proximal end to the distal end for passage of said needle, and said jaws having an opening enabling passage of the needle through tissue grasped in said jaws. This summary is not exhaustive, nor is it indicative of the scope of the present invention.

BRIEF DESCRIPTION OF THE DRAWINGS

The above and other objects and advantages of the present subject matter will become apparent from the following description and the accompanying drawings wherein.

DETAILED DESCRIPTION OF THE PREFERRED EMBODIMENTS

Figure 1A:
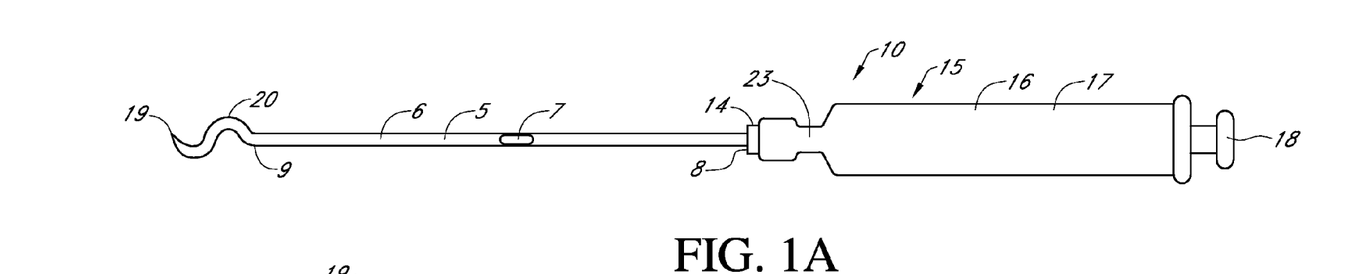
FIG. 1A is a side elevation view, partially broken away, of a first embodiment of a suture passing instrument in accordance with the invention.
Figures 1B, 1C, 2:
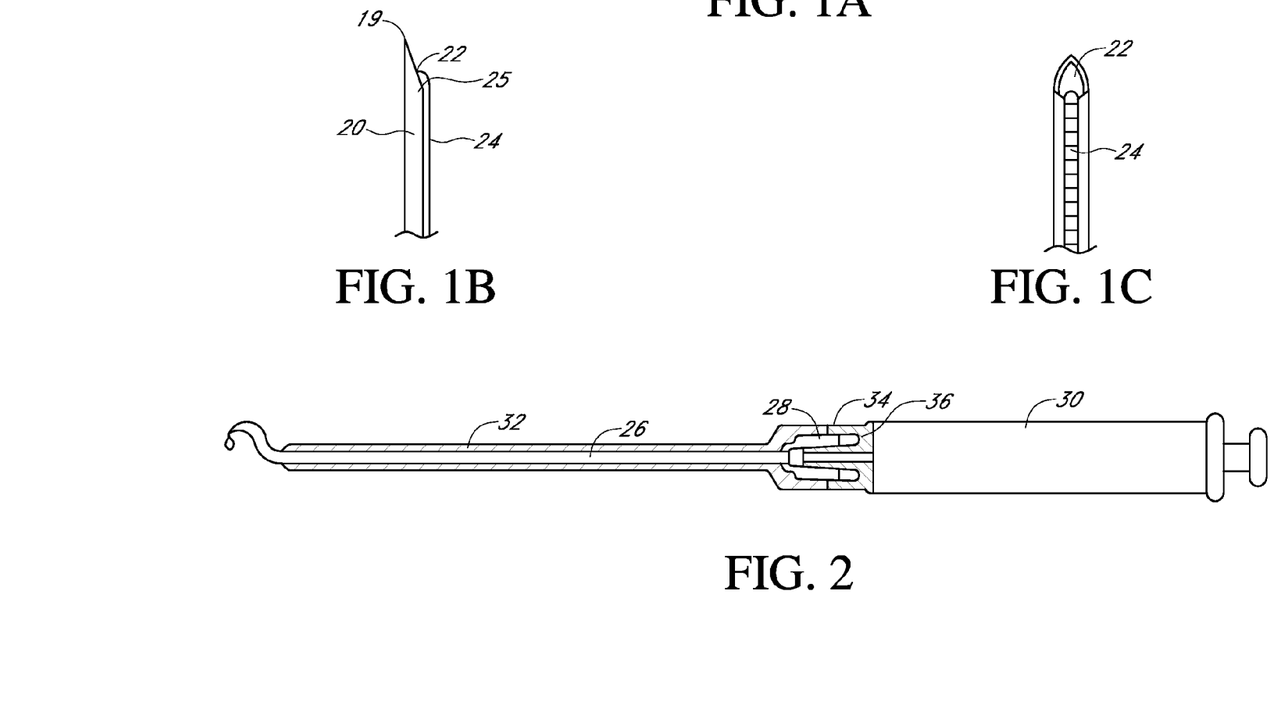
FIGS. 1B-1C is enlarged side and front elevation views respectively of the tip of the needle of FIG. 1A with a suture.
FIG. 2 is a side elevation view of an alternate embodiment of the invention.

Referring to the drawings and particularly to FIGS. 1A-1C, a suturing instrument in the form of a special needle and syringe assembly is illustrated and designated generally by the numeral 10. The needle 5 is selected or formed as a cannula 6 with a lumen 7 of sufficient size to receive a desired, or predetermined, size suture. The desired size is generally selected by a surgeon in accordance with the type of surgery to be performed. The needle 5 has a proximal end 8 and a distal end 9. Characterization of one end or the other of the needle 5 is arbitrary. For purposes of the present description, the proximal end is selected to be the end closer to the hand of a surgeon using the instrument 10.

The proximal end 8 is received in a luer lock fitting 14 of a suction device 15. A preferred form of suction device 15 is a syringe 16 having a syringe barrel 17 and a plunger 18. The syringe barrel 17 may be of a conventional construction, i.e., have a circular cross section. Alternatively, the syringe barrel 17 may have a hexagonal or other multisided cross section for easy grip and manipulation. The luer lock fitting 14 has a dimension for accommodating the needle 5. The syringe barrel 17 includes a transition channel 23 to provide for a transition from the luer lock fitting 14 to the full cross section of the syringe barrel 17. The transition channel 19 is an inlet and outlet tube for the syringe barrel 17. The distal end 9 of the needle 5 is formed with a penetrating tip 19 and a portion 20 configured for ease of passing through tissue in a confined space. In the embodiment of FIG. 1A, the end 20 is formed substantially as a corkscrew with a substantially helical configuration to enable easier manipulation and passage of the needle tip 19 through tissue in a confined space. The tip 19 may have any number of configurations including straight, as illustrated in FIGS. 1B and 1C, curved, hooked, or cork screw, as illustrated in FIG. 1A, to enable it to be easily manipulated to pass through tissue.

The tip 19 has an opening 22 which communicates the lumen 7 with the exterior of the instrument 10. The opening 22 is preferably formed by an angled cut at the end of the cannula 6. The tip 19 is at a forward, distal end of the opening 22, and the edge 25 is rearward of the opening 22. In FIGS. 1B and 1C, a suture 24 is illustrated which is in the lumen 7 and which extends through the opening 22 to the exterior of the instrument 10 where it folds over an edge 25 of the opening 22 and extends along the outer surface of the needle 5. Opening 22 is configured to enable the easy passing of a suture and the application of some force to the suture by the trailing edge of the opening without cutting the suture. The edge 25 is preferably rounded to prevent damage to the suture 24 that could result from bearing against a sharp surface. As shown in FIG. 1B, the end of the suturing needle 5 is cut at an angle providing a forward most sharp point or tip 19 for penetration of tissue.

In operation of the preferred embodiments of the present subject matter herein, the suture 24 or a portion of its total length will pass through the lumen 7 and be stored in the syringe barrel 17. In one embodiment, a suture 24 may be preloaded in the syringe barrel 17 prior to deployment through the opening 22 of the needle 5 with one end of the suture placed at the distal end of the syringe 16. In another embodiment, a suture 24 which has already been anchored to a patient may be drawn into the opening 22, through the lumen 7 and into the syringe barrel 17.

In accordance with these preferred embodiments, the plunger 18 functions to draw a length of suture 24 hydrodynamically into the needle 5 or to expel it hydrodynamically. Drawing a suture 24 into the needle 5 is accomplished by inserting an end of a suture 24 into the opening 22 of the needle 5, submerging opening 22 of the needle in water or another suitable liquid and drawing the plunger 18 back to draw a length of the suture and a quantity of water into the syringe barrel 17. A length of suture 24 is drawn by the hydraulic force of the liquid into and through the needle and in most instances into the syringe barrel 17. The suture 24 is carried by the hydrodynamic pressure resulting from the suction force generated by pulling the syringe plunger 18 outward. The needle tip 19 with suture 24 is then passed through a portion of tissue and the suture 24 is then expelled from the end of the needle and syringe by hydraulic pressure upon depressing the plunger 18. The suture 24 then extends through the tissue with opposite ends available to grasp and tie off. Additional or successive passages of the suture 24 through the tissue are accomplished in the same manner until sufficient stitching is achieved. Thus, the suture 24 is passed through the tissue by a combination of a needle and hydraulic force from the liquid in the syringe. In some forms, it may be preferable that the interior of an entry/exit tip of the syringe 16 be configured as a helical tube. Such an embodiment is disclosed below with respect to FIG. 17 below.

FIG. 2 illustrates a further embodiment in which the length of the needle may present an issue with respect to manipulatability. Certain surgical locations require a longer needle to reach the suture site. A longer needle will have a greater tendency to flex, reducing the surgeon's control over the positioning of the tip 19. The needle requires rigid support. As illustrated in FIG. 2, a needle 26 is provided with a stiffening sleeve 32. The needle 26 is covered by a stiffening sleeve 32, which extends along the length of the needle 26. The needle 26 is coupled to a syringe 30 by a luer lock connector 28. The stiffening sleeve 32 may conveniently comprise plastic molding. Materials other than plastic could also be used.

The stiffening sleeve 32 is also preferably formed with a suitable connector 34 to mate with a second or outer surface 36 on the syringe body. This connector may be a luer lock connector or other type connector. The sleeve 36 adds sufficient stiffening to a long needle 26 to enable it to be more easily manipulated in the suturing process. The needle 26 and stiffening sleeve 32 may be made of the same or different material. They may also be made simultaneously. Needle 26 may vary in length and gauge or diameter depending upon the requirements of the situation. The needle and syringe is selected to have a needle lumen of sufficient size to receive a length of suture of the desired or predetermined size and the syringe to have sufficient capacity to accommodate the length and size of suture 24.

Figures 3A, 3B, 4, 5A, 5B, 6, 7, 8:
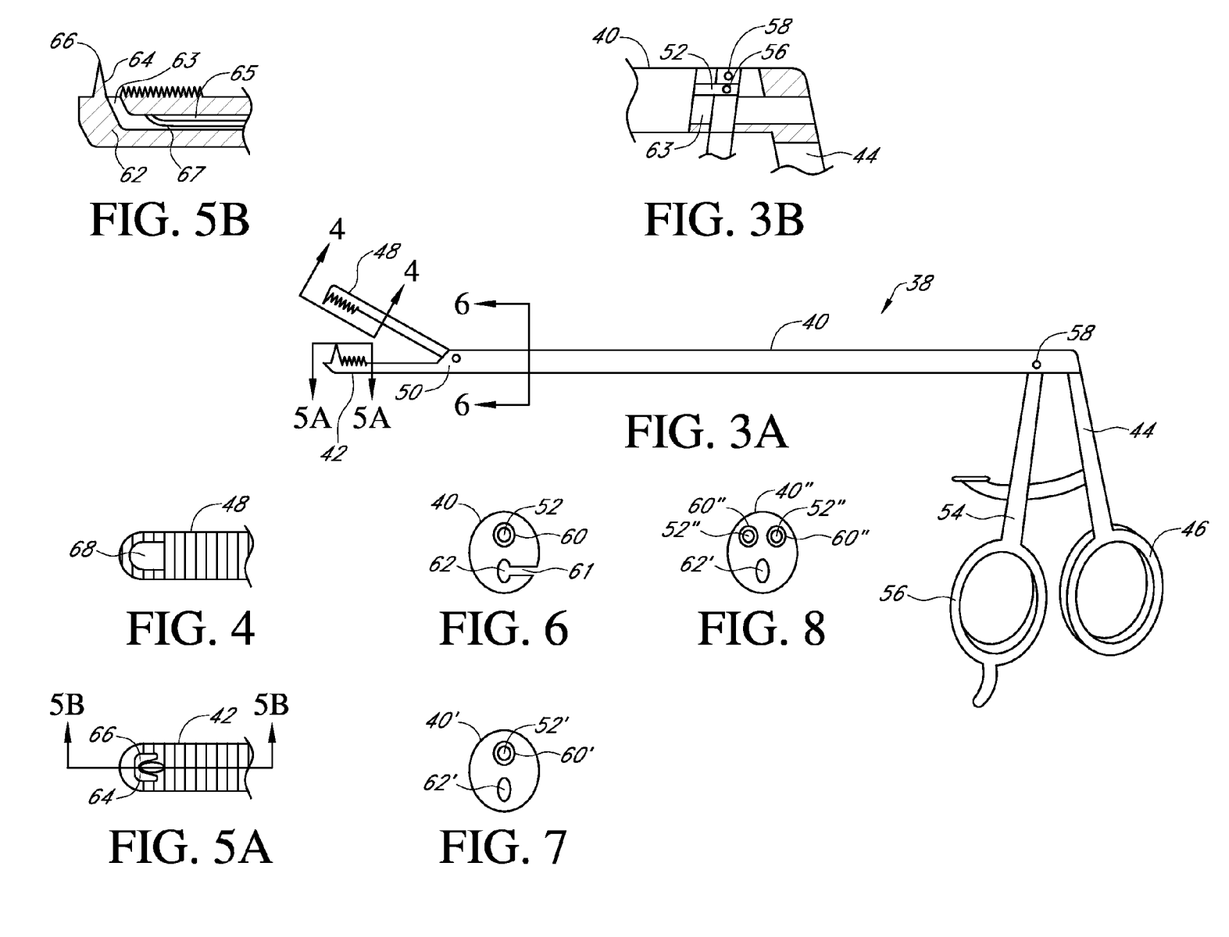
FIG. 3A is a side elevation view of another instrument of the invention.
FIG. 3B is a side elevation, partially in cross section, of the proximal end of the instrument of FIG. 3A.
FIG. 4 is a view taken on line 4-4 of FIG. 3A.
FIG. 5A is a view taken on line 5-5 of FIG. 3A.
FIG. 5B is a view taken on line 5B-5B of FIG. 5A.
FIG. 6 is a view taken on line 6-6 of FIG. 3A.
FIG. 7 is a view like FIG. 6 of an alternate embodiment of the instrument of FIG. 3A.
FIG. 8 is a view like FIG. 6 of an alternate embodiment of the instrument of FIG. 3A.

The suturing needle 5 or 26 may be used alone or in conjunction with other available instruments such as forceps or other grasping tools. It may also be used in combination with a forceps type instrument as illustrated in FIG. 3A and designated generally by the numeral 38. The instrument 38 may grip tissue, and the needle 5 or 26 may be guided through the instrument 38 as further described below. The instrument 38 comprises an elongated barrel 40 having a fixed or stationary jaw 42 at a distal end and a fixed handle 44 with a thumb ring 46 at a proximal end. A moveable jaw 48 is pivotally mounted by a pin 50 at the distal end above or opposite fixed jaw 42. The movable jaw is operated by a rod 52 (FIG. 3B) connected through a bore 60 in barrel 40 and connected to a moveable handle 54. The movable jaw 48 has an opening 68 as shown in FIG. 4 for passage of a tip and portion of the outer end of a suturing needle and a suture. The surface of the jaw is formed with cross grooves or ridges to enhance grip on tissue or a suture or the like. The moveable jaw 48 is illustrated in a plan view in FIG. 4. Moveable handle 54 has a finger ring 56 and is pivotally mounted by a pin 58 at the proximal end of barrel 40. Actuating rod 52 extends along a bore 60 extending the length of barrel 40 and is moveable by means of moveable handle 54 to open and close upper jaw 48. A second bore, a cannula 62 (FIG. 5B), extends axially along the length of barrel 40. The cannula 62 receives a needle 65 (FIG. 5B) at a proximal end. The needle 69 exits at a distal end of the cannula 62 at the lower jaw 42.

FIGS. 5A and 5B are respectively a plan view and a cross sectional elevation of the lower jaw 42. In FIG. 5B, the needle 65 has a curved tip 67 and is shown adjacent to an opening 63 at the distal end of the cannula 62. The opening 63 is positioned to face tissue (further illustrated below) grasped by the upper and lower jaws 42 and 48. At a distal end of the cannula 62 the needle 65 will engage a surface 64 of an upwardly extending wedge projection 66 on lower jaw 42. "Upwardly" here means toward tissue from the lower jaw 42. Cannula 62, as further seen in FIG. 6, has unequal orthogonal dimensions in order to receive and guide the needle 65. The cannula 62 may have an oval cross section. Other cross sections could be provided. The needle tip 67 is positioned within the cannula 62 so that it is oriented with the needle tip 67 curving upwardly. When the needle tip 67 engages wedge surface 64, it is further biased upward through a tissue grasped by the upper and lower jaws 42 and 48. The suturing procedure is further described with respect to FIGS. 10 and 11 below.

FIGS. 6, 7 and 8 are cross sectional views of alternative embodiments of the instrument 38, each having an alternate form of barrel 40. In the embodiment of FIG. 6, cannula 62 preferably has a side opening 61 to enable side release or removal of a suture. The surface projection 64 on wedge projection 66 guides the tip of a suture needle upward through a tissue that is clamped in the jaws of the forceps.

Referring to FIG. 7, an alternate barrel construction is illustrated with a barrel 40' having an actuating rod passage 60' as in the embodiment of FIG. 6. A cannula 62' has a closed oval configuration without a side slot for passage of a suture. FIG. 8 illustrates a configuration having two actuating rod passages 60" for two actuating rods 52". A cannula 62' may be incorporated or formed in the barrel 40". Alternatively, a separate cannula mounted below and extend along the barrel 40". The cannula would curve upward and extend through the lower jaw 42 at the distal end.

Figure 9:
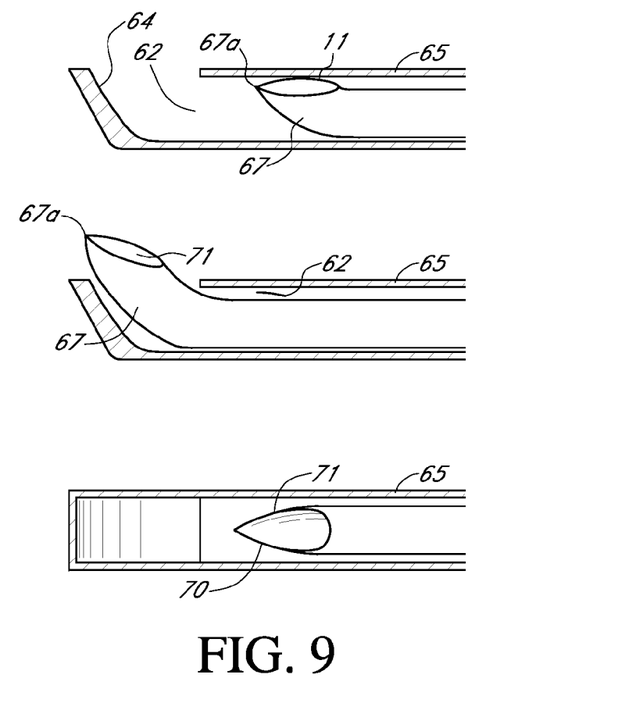
FIG. 9 illustrates an alternative form of needle interacting in the embodiment of FIGS. 3-6, and consists of FIGS. 9A, 9B and 9C respectively illustrating, partially in cross section, side elevation views, of a needle in and exiting from a cannula and a plan view of the needle in the cannula.

FIG. 9 illustrates an alternative form of needle interacting in the embodiment of FIGS. 3-6 and consists of FIGS. 9A, 9B and 9C illustrating, partially in cross section, side elevation views of the needle in and exiting from the cannula 62 and a plan view of the needle 65 in the cannula 62. In the embodiment of FIG. 9, additional means are provided to prevent the point 67a at the needle tip 67 from having motion impeded by contact with an upper surface of the cannula 62. The shape of the needle tip 67 will determine whether the needle tip 67 will slide along the upper surface of the cannula 62. It is possible for a sharp point 67a on the needle tip 67 to catch the upper surface of the cannula 62. The needle tip 67 has a periphery 70, seen in FIG. 9C, including edges which will pierce tissue. The periphery 70 also defines an opening through which sutures can pass. Contact surfaces 71 are provided on the needle 65 extending in a degree of freedom generally orthogonal to a direction of motion and in a same direction as the point 67a toward a stationary surface. The contact surfaces engage the upper surface of the cannula 62 before the point 67a of the tip 67 can. Catching of the point 67a on the upper surface of the cannula is positively prevented. Preferably, the contact surfaces 71 are formed in the periphery 70. By making the contact surfaces 71 integral with the walls of the needle 5 and the tip 67, the contact surfaces 71 do not impede piercing of tissue by the tip 67.

Figure 10:
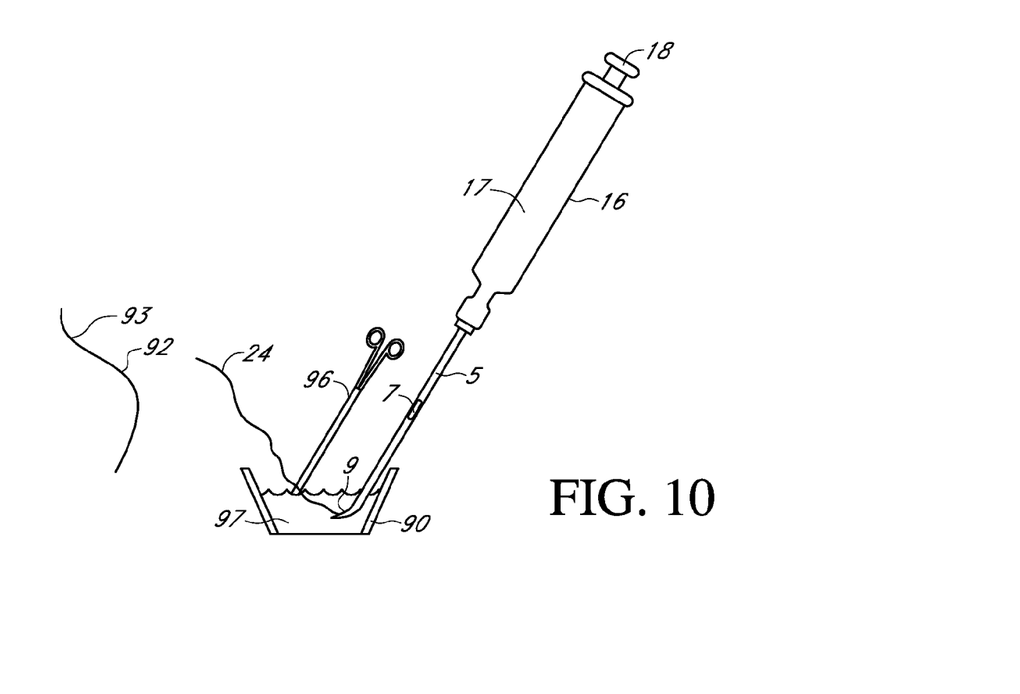
FIG. 10 illustrates the interaction of a needle, suture and a liquid reservoir.

FIG. 10 illustrates the interaction of the needle 5, the suture 24 and a liquid reservoir 90. The liquid reservoir 90 is illustrative of a liquid reservoir used in conjunction with the embodiments described above and also used in conjunction with the procedures described with respect to FIGS. 10-12. A cannula 92 is inserted into a patient 93. Various instruments may be inserted in the cannula 92 such as an arthroscope (not shown) or a forceps 96. In the present illustration, the cannula 92 is inserted into the shoulder of the patient 93. However, the present teachings apply as well to other forms of arthroscopic surgery, to laparoscopic surgery, and to other forms of non-open surgery. More than one cannula 92 may be inserted in a patient 93. A plurality of cannulas 92 may allow for the use of a number of instruments at once or may allow a surgery site to be approached from different angles.

A suture 24 may be preloaded in the syringe barrel 17. Alternatively, an anchor including an aperture may be fixed to a bone of the patient 93. A suture 24 may be threaded through the aperture to provide two free ends extending from the aperture. In the illustration of FIG. 10, the suture 24 is fixed to an anchor in a patient bone, as further illustrated with respect to FIG. 12. The forceps 96 may be inserted in the cannula 92 to grasp the free end of the suture 24. The suture 24 is then withdrawn to pull the free end of the suture 24 through cannula 92 out of the surgery site to a location exterior to the patient 93. This state is illustrated in FIG. 10.

The free end of the suture 24 and the distal end 9 of the needle 5 are placed in liquid 97 in a reservoir 98. (FIG. 10) The free end of the suture 24 is manipulated, as by handling with the forceps 96, to a position adjacent the opening 22 of the needle 5. The plunger 18 is then moved in a direction out of the syringe barrel 17. The resulting drop in pressure in the syringe barrel 17 and lumen 7 in the needle 5 draws liquid 97 into the needle 5. The free end of the suture 24 is drawn into the needle 5 by hydrodynamic force. In many uses, the plunger 18 will be withdrawn sufficiently so that the suture 24 is drawn in to the syringe barrel 17. When the plunger 18 is pressed into the syringe barrel 17, liquid 97 is expelled through the needle 5 and carries the suture 24 with it.

Figure 11A:
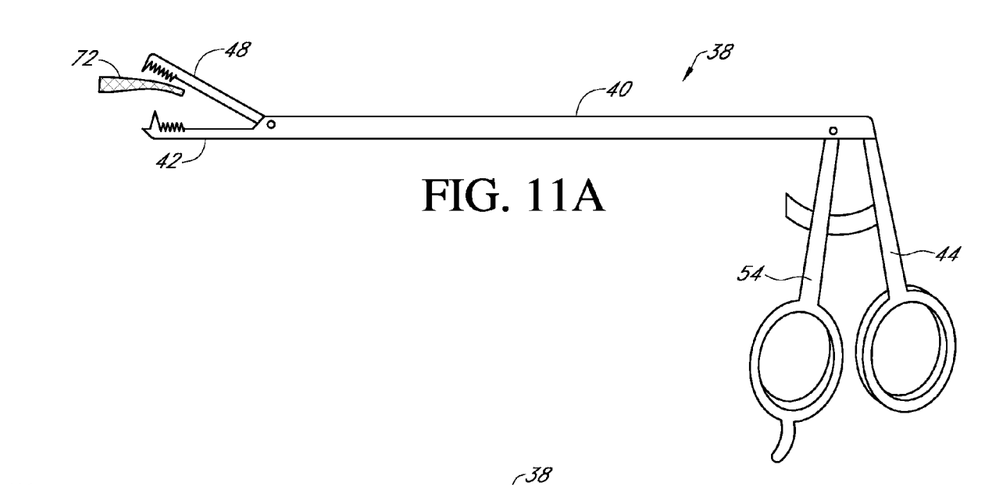
FIGS. 11A and 11B are side elevation views of the instruments of FIG. 3A and FIG. 1 respectively, shown in use.
Figure 11B:
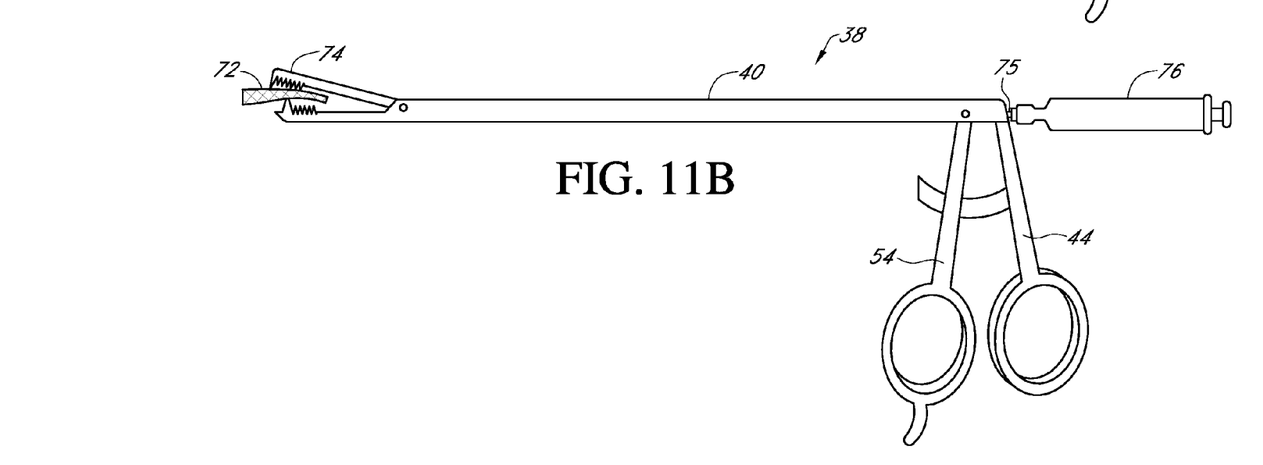

Referring to FIGS. 11A and 11B, an application is illustrated in which the suture 24 is initially within the needle and syringe assembly. The instrument 38 is illustrated in the process of grasping a piece of tissue 72 to be sutured. The tissue 72 may be within a confined space accessible through a small opening or through a tube or cannula (not shown) extending from an exterior of the patient to an area including the tissue 72. In use, the distal end of the instrument 38 is inserted through the opening, and the tissue 72 to be sutured is grasped between jaws 42 and 48. A needle 75 has a tip 74, and is attached to a syringe 76. The needle 75 is selected to have a length sufficient to pass through the cannula in the instrument 38 from the proximal end to the distal end and extend through the tissue 72. A portion of the suture 24 is loaded into the end of the needle 75 as discussed above. The needle 75 is then passed through the cannula and through the tissue 72 and then gripped by the jaws 42 and 48 of the instrument 38. The suture 24 is then expelled from the end of the needle 75 by hydraulic force from pushing the plunger of the syringe 76 forward. The end of the suture 24 is then available to grasp with a suitable tool and tie off or pass again through the tissue.

Figure 12A:
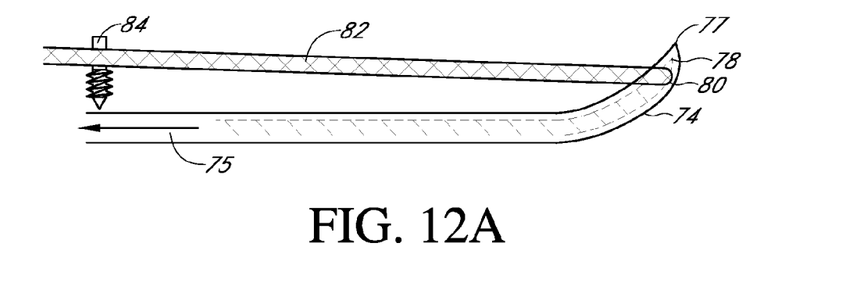
FIG. 12A-12D are enlarged partial views illustrating the loading of the needle and passing of a suture.

FIGS. 12A-12D illustrate an application in which the suture is initially outside of the needle and syringe assembly. The hollow needle 75 is illustrated having an upturned tip 74 at its distal end with a sharp point 77. A generally oval opening 78 is angled with respect to a central axis of the needle 75, and has the sharp point 77 at its distal end. A trailing edge 80 is at the rear, or proximal end of the opening 78. The trailing or aft edge 80 of the opening is formed with a radius to enable the smooth passage of a suture over it without cutting the suture. A length of suture 82 may be secured by an anchor screw 84 to a bone structure (not shown). In this illustration a piece of tissue 86 will be sutured. Initially, a free end of the suture 82 is inserted into the opening 78 of the needle 75. The end of the needle 75 with suture 82 is submerged in a quantity of liquid, and liquid and suture are drawn into the syringe along with the suture 82. The suture 82 drawn into the needle 75 is shown in FIG. 12A. The suture 82 is carried through the needle 75 and syringe 76 by the hydrodynamic pressure resulting from the suction force generated by pulling the syringe plunger outward.

Figure 12B:
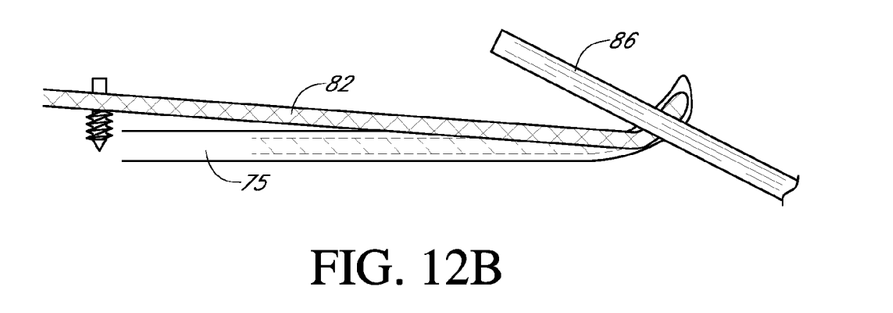
Figure 12C:
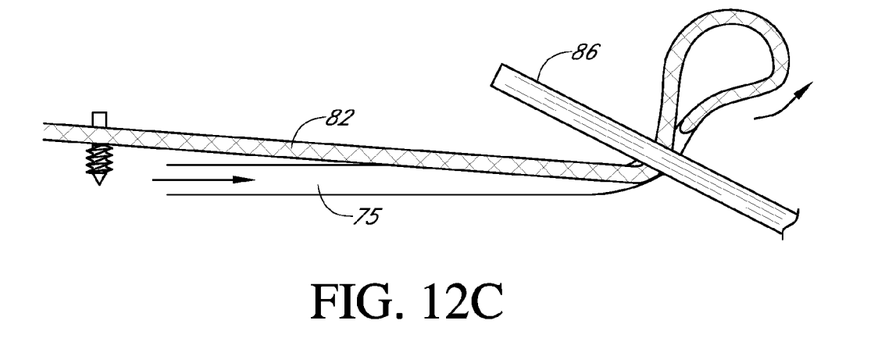
Figure 12D:
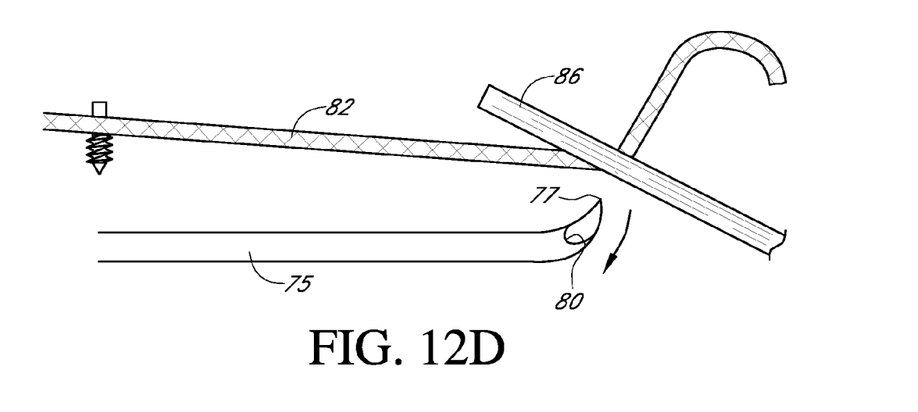

The needle 75 loaded with the suture 82 is inserted into and passed through the tissue 86 to be sutured as in FIG. 12B. Once the tip 74 of the needle 75 and opening 78 has passed through the tissue 86, the plunger of the syringe 76 is pressed forward. Consequently the suture 82 is expelled from the needle 75 by hydraulic force from the end of the needle as in FIG. 12C. The needle 75 is then withdrawn, as illustrated in FIG. 12D. The free end of the suture 82 can be grasped by forceps or other tool and tied off or reintroduced through the tissue 86 as needed. This procedure is repeated until suturing is complete.

Figure 13:
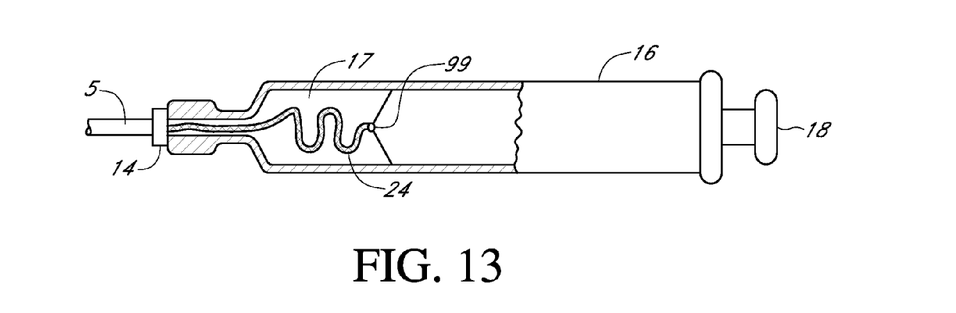
FIG. 13 is a side elevation view, partially in cross section, illustrating one embodiment in which the proximal end of the suture is restrained within the syringe.
Figure 14:
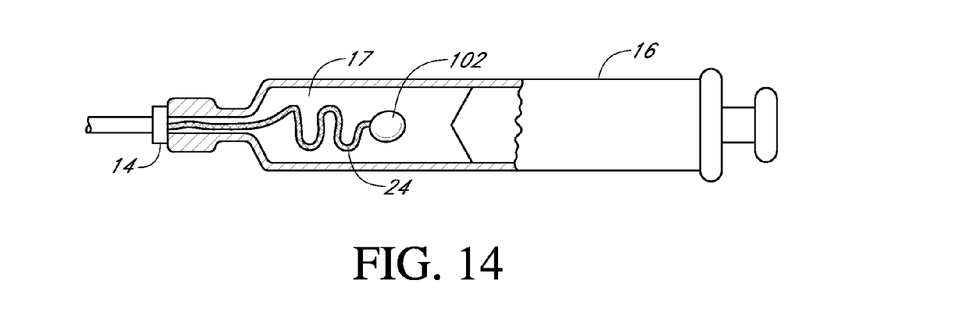
FIG. 14 is a view similar to that of FIG. 13, illustrating another embodiment in which the proximal end of the suture is restrained within the syringe.
Figure 15:
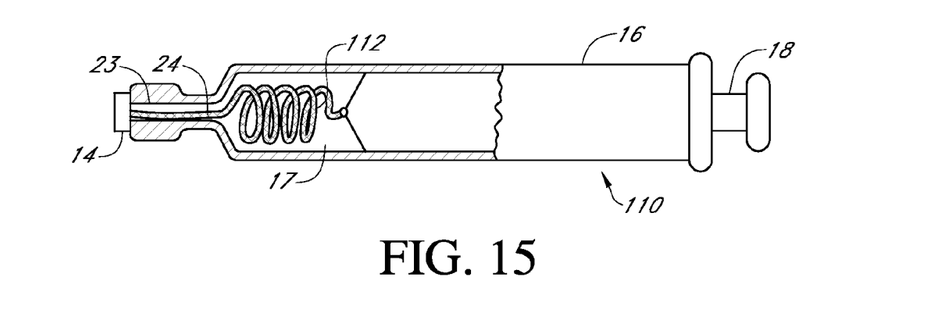
FIGS. 15 and 16 are views similar to FIGS. 13 and 14 illustrating a preloaded suture coil loaded in a syringe.
Figure 16:
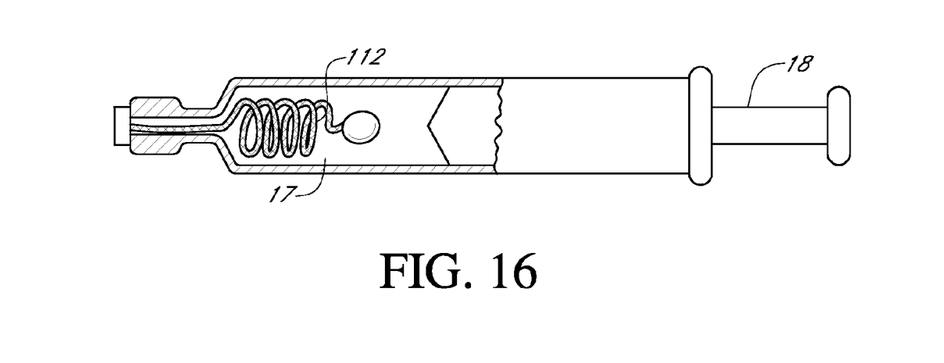
Figure 17:
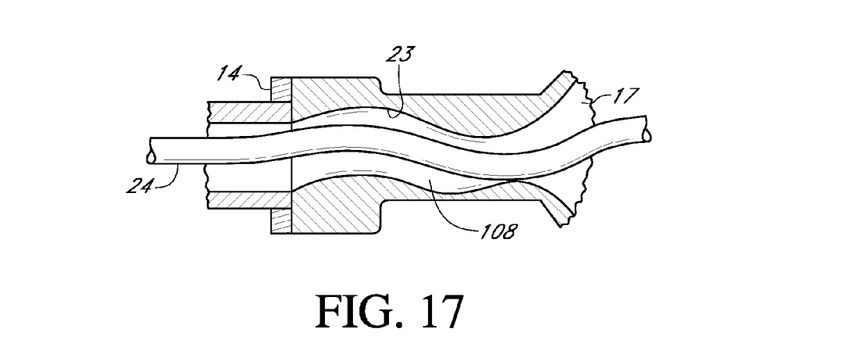
FIG. 17 is a partial detailed view, partially in cross section, illustrating one form of inlet tube through which a suture enters the syringe.

FIGS. 13-17 illustrate embodiments of syringes 16 having sutures 24 preloaded therein. In FIGS. 13-15, the needle 5 is illustrated coupled in the luer lock 14. In FIGS. 16 and 17, embodiments are illustrated in which a modular syringe 16 is provided as a subassembly which may be combined with a hollow needle. Each of these embodiments may be provided as a complete assembly 10 (FIG. 1) or as a module of an assembly 10. These embodiments may be used, for example, in conjunction with the system illustrated in FIGS. 10 and 11. A free suture, preloaded into a syringe, can be useful, convenient and time saving. In use, the proximal end of the suture 24 is usually retained within the syringe 16 as the rest of the suture 24 is let out from the syringe 16. However, it may be preferable in many instances to connect the suture 24 to the syringe 16 to positively restrain the proximal end of the suture 24 within the syringe 16. FIGS. 13 and 14 show alternative means of positively retaining the proximal end of the suture 24 within the syringe 16. In FIG. 13, the suture 24 is housed within the interior of the syringe barrel 17. The proximal end of the suture 24 is attached to a distal end of the plunger 18. Attachment may be by any convenient means, including adhesive bonding or tying the proximal end to or through a suitably shaped projection 99 on the distal end of the plunger 18.

In an alternative embodiment shown in FIG. 14, the proximal end of the suture 24 is attached to a stop 102. The stop 102 has a minimum width or diameter greater than the diameter of the inside diameter of an exit conduit 104 of the syringe 16. The stop 102 prevents the proximal end of the suture 24 from being pulled out of the syringe 16. The stop 102 may be of any convenient 3-dimensional shape. A sphere is illustrated. It is only exemplary, as the shape may be polyhedral (e.g., cubic), single- or double-curved solid (e.g., cylindrical or ellipsoidal), open-armed or structured (e.g., a caltrop or jacks shape), or any other useful shape.

FIG. 15 illustrates a syringe assembly 110 having a suture 24 stored therein formed into a coil 112. The coil 112 has a proximal end constrained to stay in the syringe 16. This constraint may be provided, for example, as in the embodiments of FIG. 13 or 14. A distal end of the suture 24 is disposed in an inlet passage 23 coupling the luer lock 14 to the syringe barrel 17. When manufactured, the syringe assembly 110 is not filled with liquid. Dry manufacture avoids issues of sealing liquid in the syringe assembly 110 during shipping and storage. Also, issues of maintaining sterility of a stored liquid are avoided. When the syringe assembly 110 is utilized, liquid is drawn into the syringe 16. This may be done in the manner described with respect to FIG. 10.

In situations in which the convenience of a preloaded syringe 16 preloaded is accommodated, the embodiment of FIG. 16 may be provided. The syringe 16 is preloaded with liquid 97. Appropriate bacteriostatic agents are included in the liquid 97. The plunger 18 is stored in its extended position. A distal end of the suture 24 is disposed in the inlet passage 23.

FIG. 17 illustrates an embodiment in which the inlet passage 23 that couples the luer lock 14 to the full diameter portion of the syringe barrel 17 has a particular shape. In this embodiment, the inlet passage 23 is a helical tube 108. As hydrodynamic pressure forces the suture 24 into the syringe barrel 17, the helical tube 108 imparts a twisting motion to the suture 24 to assist storing the suture 24 in the syringe barrel 17 in an orderly manner. The twisting motion helps the suture 24 to form a coil 112 as it is drawn in to the syringe barrel 17. Tangling of the suture 24 is avoided, and volume needed to house the suture 24 is reduced in comparison to an embodiment in which the suture 24 is stored in a disorganized form.

FIG. 18 illustrates an embodiment in which a suture 124 in a syringe 116 is directed through a needle 105, and is used to capture the free end of another suture 128. FIGS. 18A through 18E illustrate successive steps in performing this function. The suture 128 may be on an opposite side of soft tissue 130. The suture 124 comes from an opposite side of soft tissue 130. A distal end of the suture 124 is formed to have a loop 125. The loop 125 may be formed by forming a radially extending slit in an axial direction. In this embodiment, the distal end of the suture 124 including the loop 125 will have substantially the same diameter as portions of the suture 124 without the loop 125. Consequently, the suture 124 may be accommodated by a needle proportioned to the diameter of the suture 124. The loop 125 may alternatively be formed by splicing an end of the suture 124 back in to itself. In this case, a larger diameter needle is required to allow the loop 125 to pass through. Alternatively, a cannula 92 may be inserted in the tissue 130 as in the embodiment of FIG. 10.

Figure 18A:
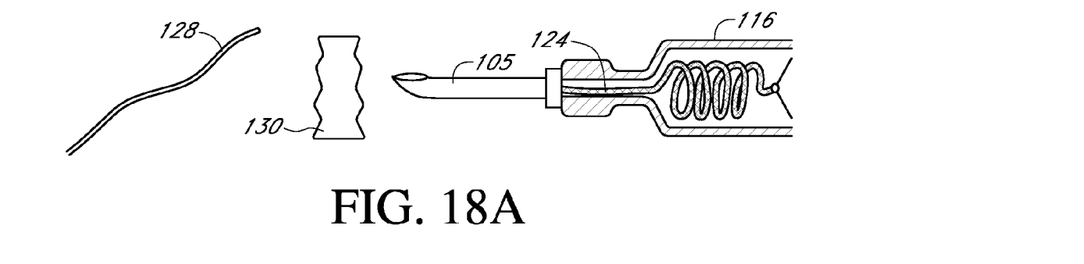
FIG. 18 is a pictorial view illustrating a method of retrieving one end of a suture during surgery.
Figure 18B:
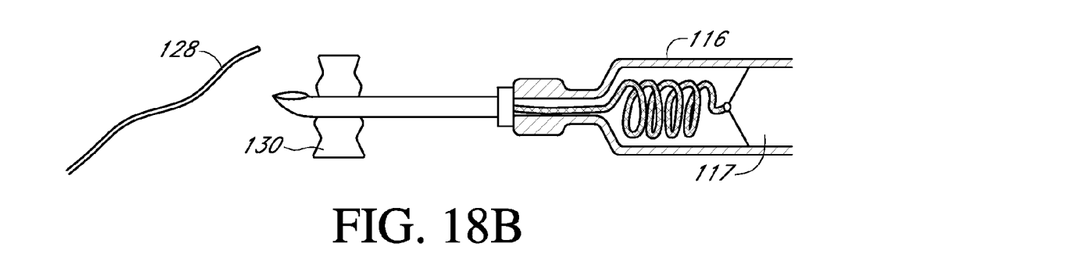
Figure 18C:
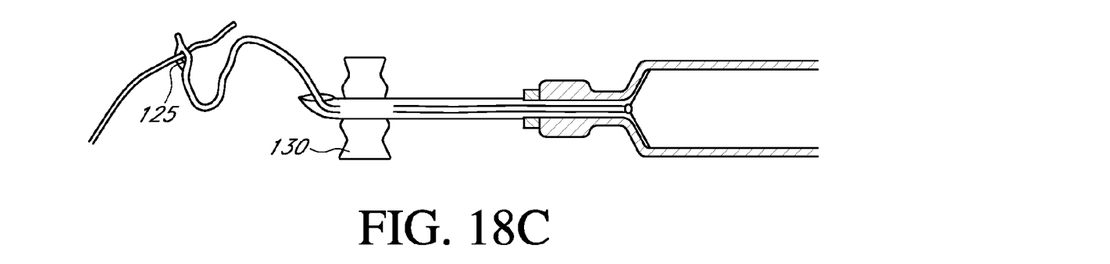
Figure 18D:
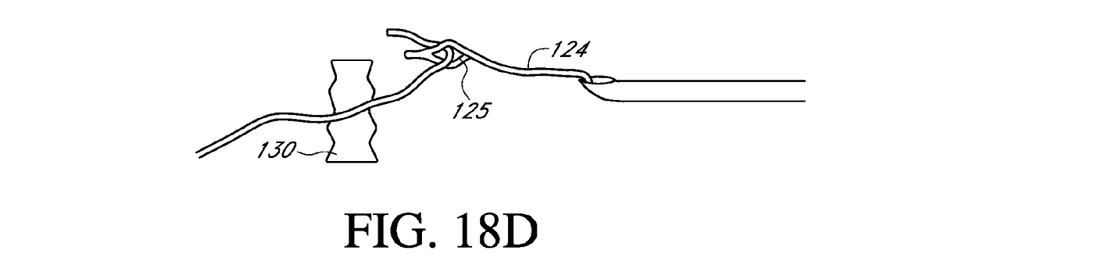
Figure 18E:
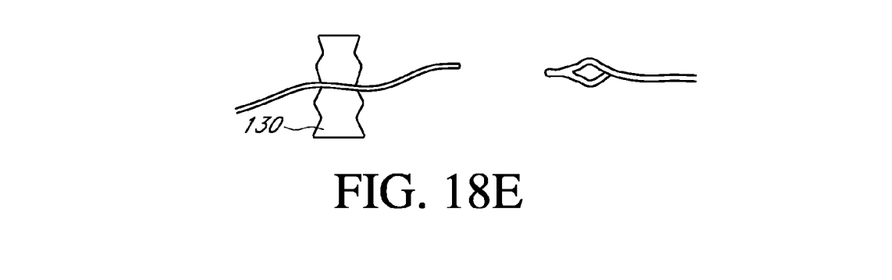

In FIG. 18a, the needle 105 is illustrated on a first side of the tissue 130. In some situations, restrictions due to anatomical topography in the operating site may not permit the use of a cannula through which a forceps can be inserted to retrieve the suture 128. In other situations, the use of a cannula may cause an unacceptable level of damage to the tissue 130. The needle 105 can penetrate the tissue 130 with minimal damage to the tissue 130, as seen in FIG. 18B. Flexibility is provided in placement of the needle 105 to the tissue 130 from different directions or different points of entry through surrounding tissue (not shown) with the simple use of a needle through the surrounding tissue without the need to insert another cannula. The needle 105 will have a smaller diameter than a cannula. A plunger of the syringe 116 may be pressed to drive the suture 124 through the needle 105 into the vicinity of the suture 128. The suture 128 is threaded through the loop 125, as illustrated in FIG. 18C. One preferred way to thread the suture 128 through the loop 125 is to withdraw them through a cannula such as the cannula 92 of FIG. 10 and perform the threading at the exterior of the patient 93. The needle 105 is withdrawn, as in FIG. 18D, and the suture 128 captured in the loop 125 is brought to the first side of the tissue 130. As illustrated in FIG. 18E, the suture 128 is removed from the loop 125, and is available for further manipulation by a surgeon.

The present subject matter being thus described, it will be apparent that the same may be modified or varied in many ways. Such modifications and variations are not to be regarded as a departure from the spirit and scope of the present subject matter, and all such modifications are intended to be included within the scope of the following claims.

I claim:

1. A syringe subassembly for connection to a needle, comprising:
   a syringe including a plunger and a chamber and an exit conduit, said plunger having a distal end mounted in said chamber for motion to draw in and expel liquid with sufficient flow to pass a suture into and out of said chamber with said liquid, said syringe subassembly substantially free of components supported to said chamber between said plunger and an outlet of said chamber; and
   a suture positioned in said chamber between said plunger and said exit conduit and having a distal end and a proximal end, said distal end of said suture positioned for passage through said exit conduit, said proximal end of said suture attached to said distal end of said plunger so as to prevent movement of said proximal end of said suture relative to said distal end of said plunger during said motion to draw in or expel liquid, and so as to prevent said proximal end of said suture from exiting said chamber.

2. A syringe subassembly according to claim 1, wherein said suture is disposed in a coil.

3. A syringe subassembly according to claim 1, further comprising liquid in said chamber to provide hydrodynamic force to move said suture and wherein said plunger is in an extended position.

4. A syringe subassembly according to claim 1, wherein said exit conduit comprises a helical tube.

5. A syringe subassembly according to claim 1, wherein a distal end of said suture has a loop formed therein.

* * * * *